United States Patent
Govari et al.

(10) Patent No.: US 8,180,430 B2
(45) Date of Patent: May 15, 2012

(54) RESOLUTION OF MAGNETIC DIPOLE AMBIGUITY IN POSITION TRACKING MEASUREMENTS

(75) Inventors: Assaf Govari, Haifa (IL); Meir Bar-tal, Zichron Ya'acov (IL); Dudi Reznick, Shimshit (IL); Doron Ludwin, Haifa (IL); Avi Shalgi, Tel-Aviv (IL); Yaron Keidar, Haifa (IL)

(73) Assignee: Biosense Webster, Inc., Diamond Bar, CA (US)

( * ) Notice: Subject to any disclaimer, the term of this patent is extended or adjusted under 35 U.S.C. 154(b) by 1663 days.

(21) Appl. No.: 11/368,243

(22) Filed: Mar. 3, 2006

(65) Prior Publication Data

US 2006/0241394 A1 Oct. 26, 2006

Related U.S. Application Data

(63) Continuation-in-part of application No. 11/063,094, filed on Feb. 22, 2005.

(51) Int. Cl.
*A61B 5/05* (2006.01)
*G01R 33/00* (2006.01)

(52) U.S. Cl. ........................... 600/424; 324/261
(58) Field of Classification Search .......... 600/407–436; 128/899; 324/200, 207.11–207.13, 260–262
See application file for complete search history.

(56) References Cited

U.S. PATENT DOCUMENTS

| | | | |
|---|---|---|---|
| 4,742,356 A * | 5/1988 | Kuipers | 342/448 |
| 5,211,165 A | 5/1993 | Dumoulin et al. | |
| 5,391,199 A | 2/1995 | Ben-Haim | |
| 5,420,379 A * | 5/1995 | Zank et al. | 178/19.03 |
| 5,443,489 A | 8/1995 | Ben-Haim | |
| 5,833,608 A * | 11/1998 | Acker | 600/409 |
| 6,147,480 A | 11/2000 | Osadchy et al. | |
| 6,161,032 A | 12/2000 | Acker | |
| 6,239,724 B1 | 5/2001 | Doron et al. | |
| 6,239,789 B1 * | 5/2001 | Sekizawa et al. | 345/173 |
| 6,261,247 B1 | 7/2001 | Ishikawa et al. | |
| 6,314,310 B1 | 11/2001 | Ben-Haim et al. | |
| 6,332,089 B1 | 12/2001 | Acker et al. | |
| 6,366,799 B1 | 4/2002 | Acker et al. | |
| 6,373,240 B1 | 4/2002 | Govari | |

(Continued)

FOREIGN PATENT DOCUMENTS

WO    WO 96/05768 A1    2/1996

OTHER PUBLICATIONS

Pending U.S. Appl. No. 11/062,258, Biosense Webster, Inc.

(Continued)

*Primary Examiner* — Francis Jaworski
(74) *Attorney, Agent, or Firm* — Louis J. Capezzuto (57) ABSTRACT

A method for position tracking includes using first and second field generators located at respective different first and second locations to generate respective first and second magnetic fields in a vicinity of first and second objects. The first and second fields are measured using first and second position sensors respectively associated with the first and second objects. First and second potential relative coordinates of the first object relative to the second object are calculated responsively to the first and second magnetic field. The potential relative coordinates are processed in order to determine a correct relative coordinate of the first object relative to the second object.

6 Claims, 5 Drawing Sheets

U.S. PATENT DOCUMENTS

| | | |
|---|---|---|
| 6,374,134 B1 * | 4/2002 | Bladen et al. .................. 600/424 |
| 6,484,118 B1 | 11/2002 | Govari |
| 6,487,516 B1 | 11/2002 | Amoral-Moriya |
| 6,493,573 B1 * | 12/2002 | Martinelli et al. ............ 600/424 |
| 6,511,147 B2 * | 1/2003 | Kubota et al. ................... 347/16 |
| 6,549,004 B1 | 4/2003 | Prigge |
| 6,618,612 B1 | 9/2003 | Acker et al. |
| 6,690,963 B2 | 2/2004 | Ben-Haim et al. |
| 6,701,179 B1 * | 3/2004 | Martinelli et al. ............ 600/424 |
| 7,174,202 B2 * | 2/2007 | Bladen et al. .................. 600/424 |
| 7,256,695 B2 * | 8/2007 | Hamel et al. ............... 340/572.1 |
| 7,525,309 B2 * | 4/2009 | Sherman et al. .............. 324/247 |
| 2002/0052604 A1 | 5/2002 | Simon et al. |
| 2002/0065455 A1 | 5/2002 | Ben-Haim et al. |
| 2003/0090424 A1 | 5/2003 | Brune et al. |
| 2003/0120150 A1 | 6/2003 | Govari |
| 2004/0068178 A1 | 4/2004 | Govari |
| 2004/0113790 A1 | 6/2004 | Hamel et al. |
| 2004/0239314 A1 | 12/2004 | Govari |
| 2005/0062469 A1 | 3/2005 | Anderson |
| 2005/0245821 A1 * | 11/2005 | Govari et al. .................. 600/429 |
| 2006/0241397 A1 * | 10/2006 | Govari et al. .................. 600/424 |

OTHER PUBLICATIONS

Pending U.S. Appl. No. 11/063,094, Biosense Webster, Inc.

Search Report EP 07 25 0883 dated Feb. 27, 2009.

* cited by examiner

RESOLUTION OF MAGNETIC DIPOLE AMBIGUITY IN POSITION TRACKING MEASUREMENTS

CROSS-REFERENCE TO RELATED APPLICATION

This application is a continuation-in-part of U.S. patent application Ser. No. 11/063,094, filed Feb. 22, 2005, which is assigned to the assignee of the present patent application and whose disclosure is incorporated herein by reference.

FIELD OF THE INVENTION

The present invention relates generally to magnetic position tracking systems, and particularly to methods and systems for resolving magnetic dipole ambiguity in position tracking measurements.

BACKGROUND OF THE INVENTION

Various methods and systems are known in the art for tracking the coordinates of objects involved in medical procedures. For example, U.S. Pat. Nos. 5,391,199 and 5,443,489, whose disclosures are incorporated herein by reference, describe systems in which the coordinates of an intrabody probe are determined using one or more field transducers. Such systems are used for generating location information regarding a medical probe, such as a catheter. A sensor, such as a coil, is placed in the probe and generates signals in response to externally-applied magnetic fields. The magnetic fields are generated by magnetic field transducers, such as radiator coils, fixed to an external reference frame in known, mutually-spaced locations. The sensor signals are processed in order to determine the coordinates of the probe in the external frame of reference.

Additional methods and systems that relate to magnetic position tracking are also described, for example, in PCT Patent Publication WO 96/05768, U.S. Pat. Nos. 6,690,963, 6,239,724, 6,618,612 and 6,332,089, and U.S. Patent Application Publications 2002/0065455 A1, 2003/0120150 A1 and 2004/0068178 A1, whose disclosures are all incorporated herein by reference. These publications describe methods and systems that track the position of intrabody objects such as cardiac catheters, orthopedic implants and medical tools used in different medical procedures.

SUMMARY OF THE INVENTION

Some position tracking systems calculate and present the relative coordinates of one object with respect to another object. An exemplary embodiment is an orthopedic system, which presents the relative coordinates of an insertion-extraction tool with respect to an orthopedic implant. Such a system enables a surgeon to approach the implant using the tool with minimal damage to surrounding tissue.

In some cases, for example when the externally-applied magnetic field is a dipole field, the relative coordinate calculation is ambiguous, providing two or more potential relative coordinates that may correspond to the correct relative coordinate.

Embodiments of the present invention provide methods and systems for resolving the ambiguous location calculations when calculating the relative coordinates between two objects. In some embodiments, first and second field generators at different locations are used to generate respective first and second magnetic fields in the vicinity of the two objects. Two position sensors respectively associated with the two objects measure the first and second fields. A-priori knowledge regarding the position of one of the position sensors relative to at least one of the field generators is combined with relative measurements of the magnetic fields by the two position sensors in order to resolve the relative coordinates unambiguously.

In a disclosed embodiment, the system calculates a first group of possible relative coordinates based on measurements of the first magnetic field made by the position sensors, and a second group of potential relative coordinates based on measurements of the second magnetic field. Since the correct relative coordinate does not depend on the location of the field generator, potential relative coordinates that do not appear in both the first group and the second group are invalidated.

The system then invalidates all but one of the remaining relative coordinates using a-priori positional information related to at least one of the field generators and at least one of the position sensors, to produce a correct relative coordinate between the two objects. In some embodiments, providing the a-priori positional information comprises fixing in advance the orientation of one of the field generators with respect to one of the objects.

In an alternative embodiment described hereinbelow, unambiguous position measurements can be performed using a single location pad having multiple field generators fixed at known offsets within the location pad.

There is therefore provided, in accordance with an embodiment of the present invention, a method for position tracking, including:

using first and second field generators located at respective different first and second locations, generating respective first and second magnetic fields in a vicinity of first and second objects;

measuring the first and second fields using first and second position sensors respectively associated with the first and second objects;

calculating first potential relative coordinates of the first object relative to the second object responsively to the first magnetic field, and second potential relative coordinates of the first object relative to the second object responsively to the second magnetic field; and processing the first and second potential relative coordinates in order to determine a correct relative coordinate of the first object relative to the second object by:

comparing the first potential relative coordinates to the second potential relative coordinates; and comparing at least one of the first and second potential relative coordinates to a-priori positional information with respect to at least one of the field generators and at least one of the position sensors.

In a disclosed embodiment, one of the first and second objects includes an implant inserted into a body of a patient, wherein the other of the first and second objects includes a tool, and processing the first and second potential relative coordinates includes tracking a relative position of the tool with respect to the implant.

In some embodiments, processing the first and second potential relative coordinates includes invalidating a relative coordinate value in one of the first and second potential relative coordinates that does not appear in the other of the first and second potential relative coordinates. Additionally or alternatively, processing the first and second potential relative coordinates includes invalidating a relative coordinate value in at least one of the first and second potential relative coordinates responsively to an inconsistency between the relative coordinate value and the a-priori positional information.

In a disclosed embodiment, the method includes providing the a-priori positional information by positioning the at least one of the field generators so as to cause at least one of the magnetic fields to have a known orientation with respect to the at least one of the position sensors. Typically, positioning the at least one of the field generators includes marking the at least one of the field generators with a mark indicative of the orientation of the at least one of the magnetic fields.

In another embodiment, the method includes providing the a-priori positional information by positioning the first field generator at a first distance from the first object along an axis, positioning the second field generator on an opposite side of the first object along the axis at a second distance from the first object different from the first distance, so as to cause the first and second fields measured at the first object to have different magnitudes.

In yet another embodiment, in which the first and second field generators have respective first and second axes, the method includes providing the a-priori positional information by positioning the first and second field generators at a known distance from one another and so that the first and second axes are parallel.

In still another embodiment, the method includes providing the a-priori positional information by defining a working volume specifying a valid range of location coordinates of the first and second objects, and positioning the first field generator at a sufficient distance from the first and second objects so that at least one of the first and second potential relative coordinates falls outside the working volume.

Typically, the first and second magnetic fields include at least one of dipole and semi-dipole magnetic fields.

There is also provided, in accordance with an embodiment of the present invention, a method for position tracking, including:

using a co-axial pair of first and second field generators fixed at a respective known offset from one another along a common axis in a location pad, generating respective first and second magnetic fields in a vicinity of an object;

measuring the first and second magnetic fields using a position sensor associated with the object; and calculating unambiguous position coordinates of the object with respect to the location pad based on the measured first and second magnetic fields and the known offset.

In some embodiments, the method includes generating additional magnetic fields using one or more additional co-axial pairs of field generators fixed at respective known offsets from one another along respective different axes, and measuring the additional magnetic fields by the position sensor, wherein calculating the unambiguous position coordinates includes calculating the coordinates responsively to the measured additional magnetic fields and the respective known offsets.

Typically, generating the first and second magnetic fields includes driving the first and second field generators with respective first and second drive signals having respective different first and second frequencies.

There is additionally provided, in accordance with an embodiment of the present invention, a position tracking system, including:

first and second field generators located at respective different first and second locations, which are arranged to generate respective first and second magnetic fields in a vicinity of first and second objects;

first and second position sensors respectively associated with the first and second objects, which are arranged to measure the first and second fields;

a processor, which is arranged to calculate first potential relative coordinates of the first object relative to the second object responsively to the first magnetic field, to calculate second potential relative coordinates of the first object relative to the second object responsively to the second magnetic field, and to process the first and second potential relative coordinates in order to determine a correct relative coordinate of the first object relative to the second object by comparing the first potential relative coordinates to the second potential relative coordinates, and comparing at least one of the first and second potential relative coordinates to a-priori positional information with respect to at least one of the field generators and at least one of the position sensors.

There is further provided, in accordance with an embodiment of the present invention, a position tracking system, including:

a location pad including a co-axial pair of first and second field generators fixed at a known offset from one another along a common axis, which are arranged to generate respective first and second magnetic fields in a vicinity of an object;

a position sensor associated with the object, which is arranged to measure the first and second magnetic fields; and a processor, which is arranged to calculate unambiguous position coordinates of the object with respect to the location pad based on the measured first and second magnetic fields and the known offset.

There is moreover provided, in accordance with an embodiment of the present invention, a computer software product used in a position tracking system, the product including a computer-readable medium, in which program instructions are stored, which instructions, when read by a computer, cause the computer to control first and second field generators located at respective different first and second locations so as to generate respective first and second magnetic fields in a vicinity of first and second objects, to accept measurements of the first and second fields from first and second position sensors respectively associated with the first and second objects, to calculate first potential relative coordinates of the first object relative to the second object responsively to the first magnetic field, to calculate second potential relative coordinates of the first object relative to the second object responsively to the second magnetic field, and to process the first and second potential relative coordinates in order to determine a correct relative coordinate of the first object relative to the second object by comparing the first potential relative coordinates to the second potential relative coordinates, and comparing at least one of the first and second potential relative coordinates to a-priori positional information with respect to at least one of the field generators and at least one of the position sensors.

The present invention will be more fully understood from the following detailed description of the embodiments thereof, taken together with the drawings in which:

DETAILED DESCRIPTION OF EMBODIMENTS

System Description

In typical magnetic-based position sensing systems, such as the systems cited in the above-mentioned references, externally-generated magnetic fields induce position-responsive electrical currents in a receiver, such as a sensor coil, that is located within a sensor unit. In medical applications of such systems, the sensor unit is fitted inside a medical implant, a probe or another medical tool. A sensor control unit internal to the sensor unit acquires the signals from the receiver, computes position information, and transmits the information to the external system. The external system calculates the location and orientation of the sensor unit based on the position information received from the sensor unit.

Figure 1:
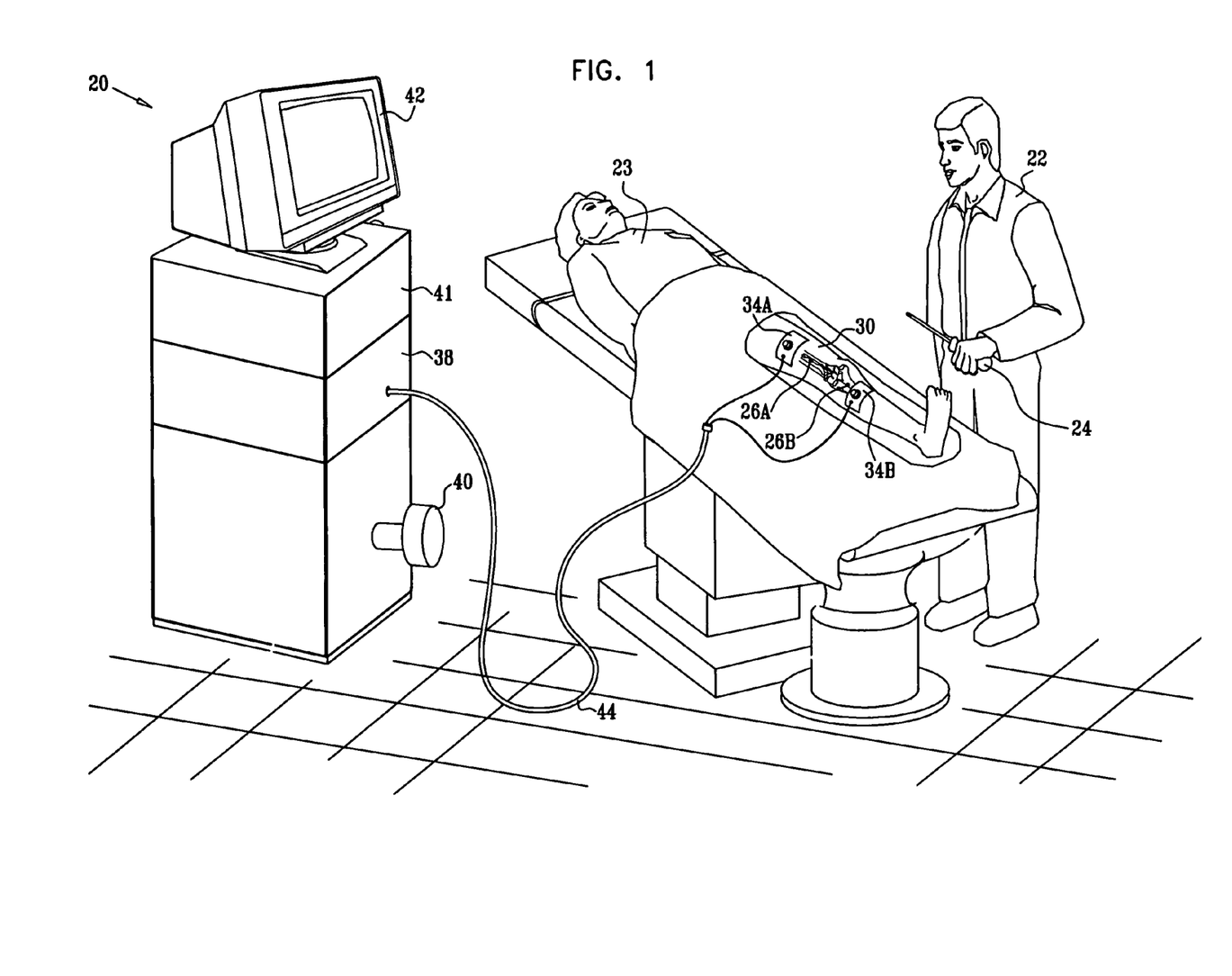
FIG. 1 is a schematic, pictorial illustration of a magnetic position tracking system used in surgery, in accordance with an embodiment of the present invention.

FIG. 1 is a schematic, pictorial illustration of a magnetic position tracking system 20 used in surgery, in accordance with an embodiment of the present invention. A surgeon 22 performs a medical procedure on a patient 23 using a medical tool 24. Orthopedic implants 26, marked 26A and 26B, are introduced into the patient's body at a surgical site, which is located in this example in a leg 30 of the patient. The tracking system guides the surgeon in performing the procedure, in this example a knee-joint operation, by measuring and presenting the positions of implants 26 and tool 24. The system measures the location and orientation coordinates throughout a working volume that comprises the surgical site.

In particular, system 20 calculates and presents the relative position coordinates of tool 24 with respect to one of implants 26 (or both). For example, in some embodiments, tool 24 comprises an insertion tool used to insert and/or extract implants 26 into and out of the bone. By presenting the relative coordinates of tool 24 with respect to the implant, the position tracking system aids the surgeon in accurately approaching the implant with the tool, thus minimizing the damage caused to the surrounding tissue.

Additionally or alternatively, the calculation and presentation of relative coordinates can be desirable in other situations or applications, such as navigation of spine pedicle screws in spine surgery and navigation of a catheter relative to a reference patch.

The coordinates of tool 24 and implants 26 are measured using field generators, such as location pads 34. Location pads 34 may be attached to the patient's body or positioned using any suitable external fixture. In the example of FIG. 1, two pads marked 34A and 34B are placed on the patient's calf and thigh in proximity to implants 26A and 26B. A signal generator unit 38 generates drive signals that drive location pads 34. Pads 34 typically comprise field generating coils that generate magnetic fields throughout the working volume responsively to the drive signals. The location pads are typically connected by cables 44 to unit 38, although a wireless connection is also feasible.

Implants 26 and tool 24 contain miniature, wireless sensor units, which are described in detail hereinbelow. Each sensor unit comprises a position sensor that is designed to sense the magnetic field in its vicinity. The magnetic fields generated by location pads 34 induce currents in the position sensors of the sensor units fitted into tool 24 and implants 26. In response to the induced currents, control and communication circuits in each sensor unit generate and transmit position signals that are indicative of the location and orientation of the implant or tool. Wireless sensor units can also be fitted into various temporary marker devices, such as a marker device temporarily inserted into a bone and removed following the procedure.

The position signals are received by a wireless control unit 40, which is coupled to a computer 41. Computer 41 serves as the main system controller of system 20. In some embodiments, computer 41 processes the received signals and calculates the relative position (location and orientation) coordinates of tool 24 with respect to implants 26, regardless of their positions with respect to the location pads. The results are typically presented to the surgeon on a display 42.

Typically, computer 41 comprises a general-purpose computer, which is programmed in software to carry out the functions described herein. The software may be downloaded to the computer in electronic form, over a network, for example, or it may alternatively be supplied to the computer on tangible media, such as CD-ROM. Computer 41 may be implemented as a standalone unit, or it may alternatively be integrated with other components of system 20.

The system shown in FIG. 1 is related to an orthopedic application. Further details regarding position tracking systems of this sort can be found in the above-mentioned U.S. patent application Ser. No. 11/063,094. Another, similar system for orthopedic applications, in which the principles of the present invention may be implemented, is described in U.S. Provisional Patent Application No. 60/550,924, filed Mar. 5, 2004, now filed as U.S. patent application Ser. No. 11/062,258 filed Feb. 18, 2005. All of these applications are assigned to the assignee of the present patent application, and their disclosures are incorporated herein by reference.

As will be explained in detail hereinbelow, the field strength measurements performed by the position sensors sometimes lead to ambiguous location calculations. The methods and systems described below resolve these ambiguities to provide the true relative location of the tool with respect to the implant.

Figure 2:
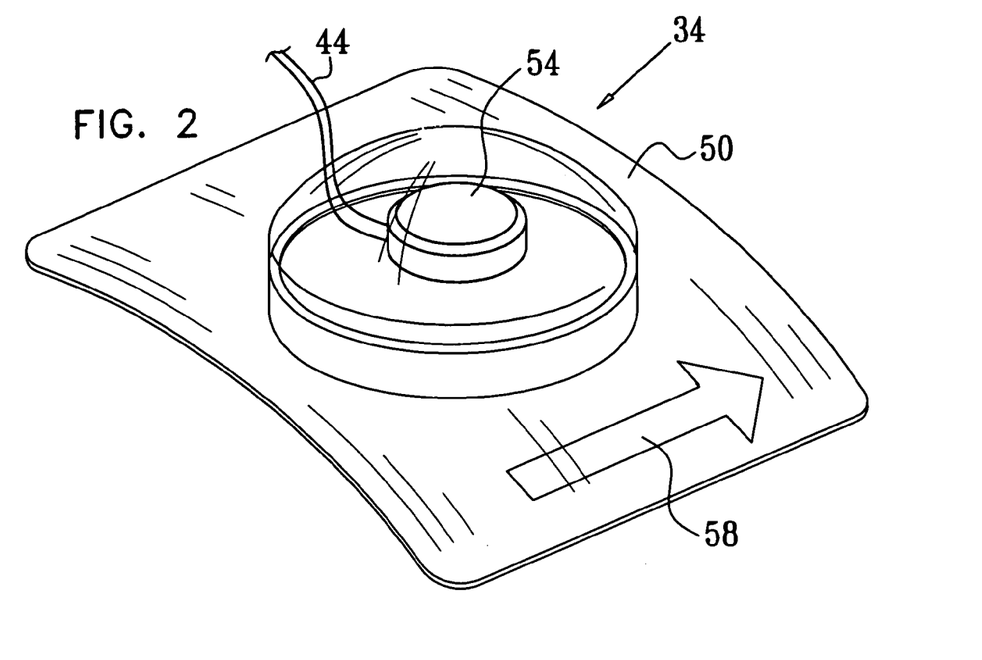
FIG. 2 is a schematic, pictorial illustration of a location pad, in accordance with an embodiment of the present invention.

FIG. 2 is a schematic, pictorial illustration of location pad 34, in accordance with an embodiment of the present invention. Pad 34 comprises a base 50, which is used for attaching the location pad to the patient's body. The location pad comprises at least one field generating coil 54, which generates a dipole or semi-dipole magnetic field responsively to the drive signals transmitted through cable 44. In some embodiments, an arrow 58 marked on pad 34 is aligned in a known direction with respect to the magnetic field generated by the location pad. Arrow 58 assists in resolving measurement ambiguity, as will be explained below.

Figure 3:
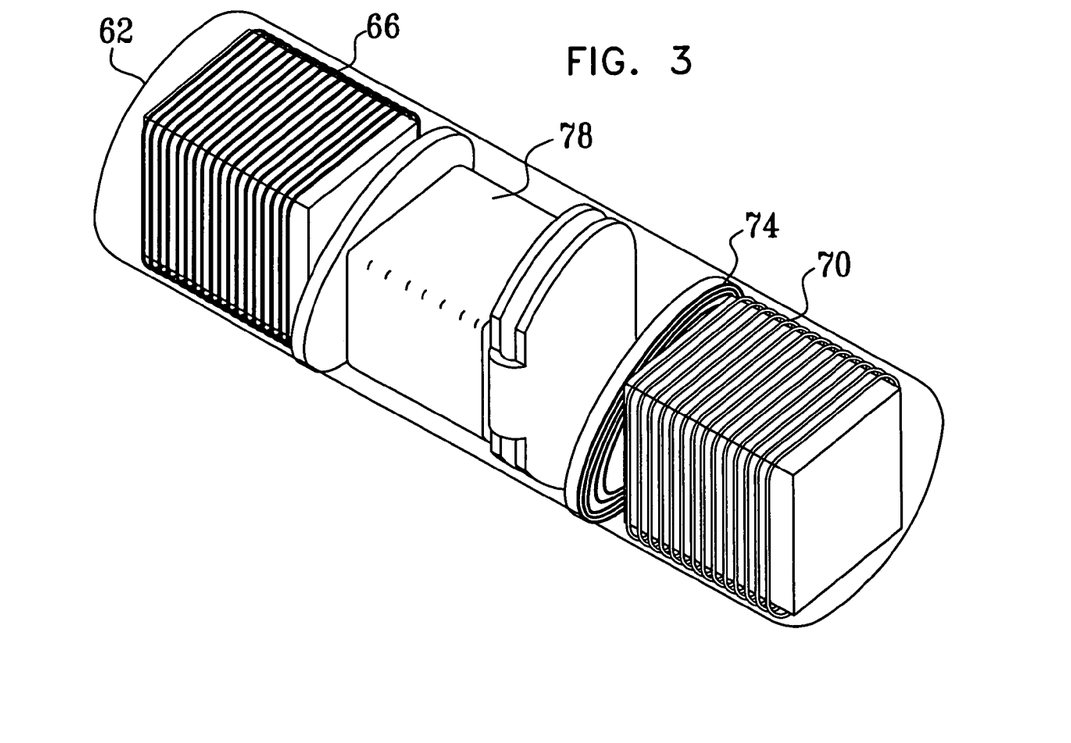
FIG. 3 is a schematic, pictorial illustration of a sensor unit, in accordance with an embodiment of the present invention.

FIG. 3 is a schematic, pictorial illustration of a sensor unit 62 that is contained in implants 26 and in tool 24, in accordance with an embodiment of the present invention. Sensor unit 62 comprises a position sensor 66, typically comprising three field sensing coils that sense the applied magnetic fields in the vicinity of the sensor unit. In some embodiments, power coils 70 serve as a power source for sensor unit 62. The power coils typically receive radio frequency (RF) energy by inductive coupling from an external driving antenna (which may be a part of wireless control unit 40 shown in FIG. 1).

Alternatively, power may be supplied by a battery (not shown) in sensor unit 62 or by other suitable means. A communication coil 74 is used to transmit the position signals from the sensor unit to wireless control unit 40. Alternatively, either the coils of sensor unit 62 or power coils 70 may also be used for transmitting the position signals, obviating the need for the separate communication coil.

Position sensor 66 and coils 70 and 74 are coupled to a sensor control unit 78. The magnetic fields generated by location pads 34 induce time-varying signal voltages across the field sensing coils in position sensor 62, as described above. Unit 78 receives the signal voltages and generates position signals in response to these voltages. Unit 78 drives communication coil 74 to transmit the position signals to a receiving antenna in the external system, typically in wireless control unit 40. FIG. 3 shows an exemplary sensor unit configuration. As noted above, any other suitable electrical and/or mechanical configuration can be used to implement sensor unit 62 to suit different medical implants and tools.

Ambiguity in Position Measurements

In the description that follows, it is assumed that the magnetic field generated by field generating coils 54 in location pads 34 are substantially dipole magnetic fields. It is also assumed that position sensor 62 measures the three orthogonal components of the magnetic field (for example by using three field sensing coils oriented along three mutually-orthogonal axes). Under these assumptions, the location coordinates of sensor 62 with respect to a particular location pad can be determined by solving the following three equations:

$$B_x = \frac{-2x^2 + y^2 + z^2}{(x^2 + y^2 + z^2)^{5/2}} \quad [1]$$

$$B_y = \frac{-3xy}{(x^2 + y^2 + z^2)^{5/2}} \quad [2]$$

$$B_z = \frac{-3xz}{(x^2 + y^2 + z^2)^{5/2}} \quad [3]$$

wherein $B_x$, $B_y$, and $B_z$ respectively denote the x-, y-, and z-axis components of the dipole magnetic field generated by field generating coil 54. Without loss of generality, the magnetic dipole is assumed to be oriented along the x-axis. Coordinates x, y and z denote the three location coordinates of the position sensor relative to the field generating coil.

During the operation of system 20, position sensor 62 in either tool 24 or implant 26 measures $B_x$, $B_y$ and $B_z$. In some embodiments, computer 41 solves equations [1]-[3] above to derive the x, y, and z location coordinates of sensor 62 relative to pad 34. Because of the symmetry of the dipole field, for any {x,y,z} location coordinate that solves equations [1]-[3] above, the location coordinate given by {-x,-y,-z} is also a solution. The {-x,-y,-z} location coordinate is referred to as a mirror coordinate. These ambiguities in the location calculation may lead to ambiguous and/or erroneous position tracking measurements in system 20.

Figure 4:
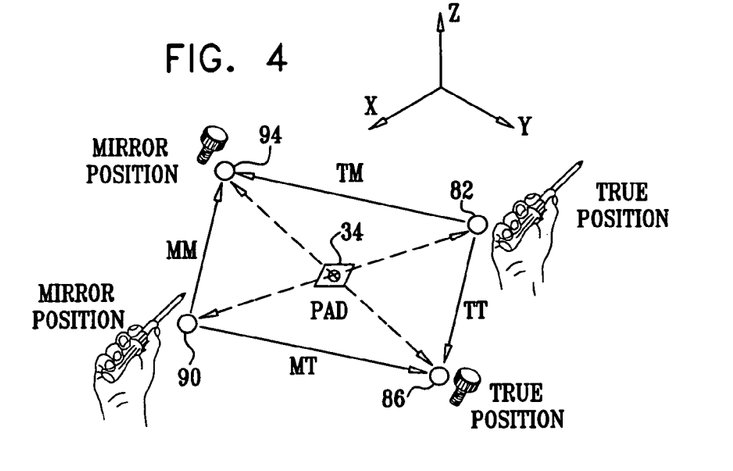
FIG. 4 is a diagram that schematically illustrates ambiguous position measurements, in accordance with an embodiment of the present invention.

FIG. 4 is a diagram that schematically illustrates ambiguous position measurements, in accordance with an embodiment of the present invention. FIG. 4 demonstrates the true and mirror location coordinates of position sensors of a single tool 24 and a single implant 26, both measuring the field generated by a single location pad 34.

The position sensor in tool 24 measures the field generated by pad 34. Based on this measurement, computer 41 calculates two solutions of equations [1]-[3] above. One of these solutions corresponds to a true location coordinate 82 of tool 24, and the other solution corresponds to a mirror location coordinate 90 of the tool. Given the available measured information, computer 41 has no way of determining which of the two solutions corresponds to the correct location of the tool.

The position sensor in implant 26 also measures the field generated by pad 34, and computer 41 derives two solutions of equations [1]-[3] based on this measurement. One of these two solutions corresponds to a true location coordinate 86 of implant 26. The other solution corresponds to a mirror location coordinate 94 of the implant. Again, computer 41 has no way of determining which of the two solutions corresponds to the correct location of the implant.

As noted above, computer 41 calculates and presents the relative location coordinate of tool 24 with respect to implant 26. Because of the ambiguous location calculation, computer 41 should consider four potential relative locations coordinates, marked as vectors TT, MM, MT and TM in FIG. 4. Vector TT denotes the relative location of the true location of the tool with respect to the true location of the implant. Vector MM denotes the relative location of the mirror location of the tool with respect to the mirror location of the implant. Vector TM denotes the relative location of the true location of the tool with respect to the mirror location of the implant. Finally, vector MT denotes the relative location of the mirror location of the tool with respect to the true location of the implant. Based on the available information, computer 41 has no way of determining which of the four vectors corresponds to the correct relative location coordinate of tool 24 with respect to implant 26.

Ambiguity Resolution Method

In some embodiments, system 20 uses two location pads 34, as well as a-priori positional information related to at least one of the location pads and at least one of the position sensors, in order to resolve the ambiguous location calculation and determine the correct relative location coordinate of tool 24 with respect to implant 26.

Figure 5:
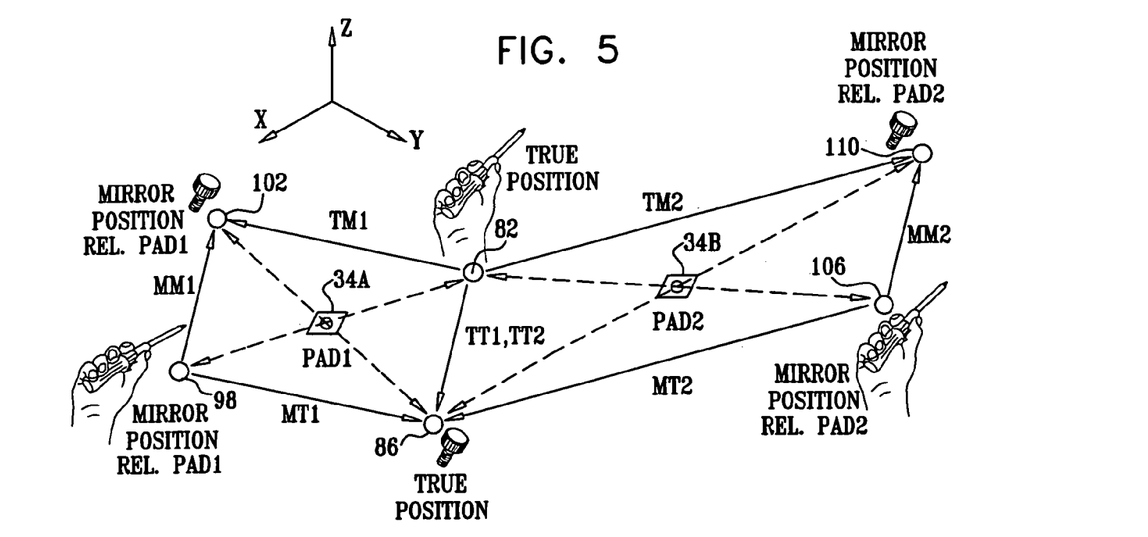
FIG. 5 is a diagram that schematically illustrates ambiguous position measurements, in accordance with another embodiment of the present invention.

FIG. 5 is a diagram that schematically illustrates ambiguous position measurements relative to two location pads 34, in accordance with an embodiment of the present invention. The figure shows the different true and mirror coordinates of a single tool 24 and a single implant 26, with respect to two location pads 34A and 34B (denoted PAD1 and PAD2, respectively). The following table lists the six coordinates shown in the figure:

| Figure reference | Description |
| --- | --- |
| 82 | True location coordinate of tool 24 |
| 86 | True location coordinate of implant 26 |
| 98 | Mirror location coordinate of tool 24 relative to location pad 34A (PAD1) |
| 102 | Mirror location coordinate of implant 26 relative to location pad 34A (PAD1) |
| 106 | Mirror location coordinate of tool 24 relative to location pad 34B (PAD2) |
| 110 | Mirror location coordinate of implant 26 relative to location pad 34B (PAD2) |

As a result of the ambiguous location calculation, computer 41 should consider eight potential relative coordinates of tool 24 with respect to implant 26. The eight potential relative coordinates are listed in the following table:

| Figure reference | Description |
| --- | --- |
| TT1 | True location of tool relative to true location of implant, measured using the field of PAD1 |
| MM1 | Mirror location of tool relative to mirror location of implant, measured using the field of PAD1 |
| TM1 | True location of tool relative to mirror location of implant, measured using the field of PAD1 |
| MT1 | Mirror location of tool relative to true location of implant, measured using the field of PAD1 |
| TT2 | True location of tool relative to true location of implant, measured using the field of PAD2 |
| MM2 | Mirror location of tool relative to mirror location of implant, measured using the field of PAD2 |
| TM2 | True location of tool relative to mirror location of implant, measured using the field of PAD2 |
| MT2 | Mirror location of tool relative to true location of implant, measured using the field of PAD2 |

Four of the relative coordinates (TT1, MM1, TM1 and MT1) were measured using the magnetic field of PAD1. These vectors are referred to as belonging to group 1. The remaining four vectors (TT1, MM1, TM1 and MT1) were measured using the field of PAD2, and are referred to as belonging to group 1.

Figure 6:
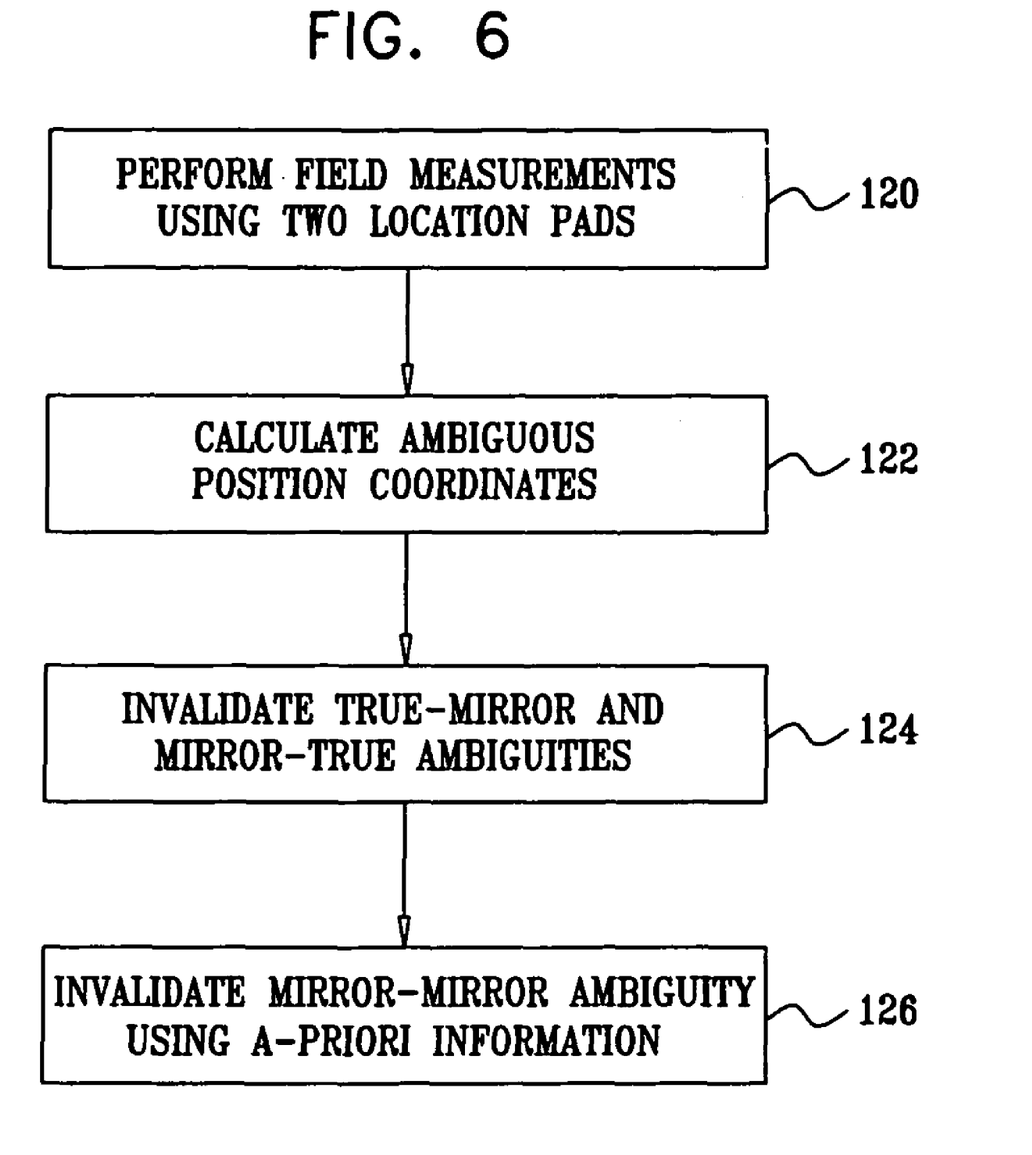
FIG. 6 is a flow chart that schematically illustrates a method for resolving measurement ambiguity, in accordance with an embodiment of the present invention.

FIG. 6 is a flow chart that schematically illustrates a method for resolving measurement ambiguity, in accordance with an embodiment of the present invention. The method begins with system 20 performing field measurements using two location pads 34, at a measurement step 120. Using the field measurements, computer 41 calculates the potential relative coordinate vectors, at a potential vector calculation step 122. In the embodiment described in FIG. 5 above, for example, computer 41 calculates the eight vectors denoted TT1, TM1, MT1, MM1, TT2, TM2, MT2 and MM2.

Computer 41 now invalidates potential relative coordinates that are not similarly measured by both location pads, at a first ambiguity resolution step 124. The reasoning behind this mechanism is that the correct relative coordinate value does not depend on the location or the identity of the location pad used to measure it. Therefore, the correct relative coordinate should be measured similarly (i.e., within an acceptable tolerance margin related to measurement errors) using the fields of PAD1 and PAD2.

In other words, computer 41 can invalidate, or rule out, any vector that does not appear in both group 1 and group 2. If a certain vector does appear in both group 1 and group 2, it may (but not necessarily) correspond to the correct relative coordinate. Thus, in step 124, computer 41 compares the vectors in groups 1 and 2 and considers only vectors that appear in both groups. For example, examining FIG. 5 above, it can be seen that half of the vectors (namely vectors TM1, MT1, TM2 and MT2) can be invalidated. None of these vectors have a similar counterpart in the opposite group.

However, even after invalidating the TM and MT vectors, some ambiguity still remains to be resolved. Specifically, vector TT1 in group 1 is similar to vector TT2 in group 2, and vector MM1 in group 1 is similar to vector MM2 in group 2. In order to resolve the remaining ambiguity, computer 41 uses a-priori positional information related to at least one of the position sensors relative to at least one of the location pads, at a second ambiguity resolution step 126. Computer 41 invalidates potential relative coordinates that are inconsistent with the a-priori positional information.

One exemplary method of providing this a-priori information is fixing in advance the orientation of one of the location pads with respect to one of the implants. In some embodiments, the surgeon attaches one of the location pads so that arrow 58 marked on this pad points in the direction of one of the implants.

Without loss of generality, assume that arrow 58 of the pad points along the positive direction of the x-axis. Using this information, computer 41 can invalidate any vector having a negative x-axis component. In the example of FIG. 5 above, the a-priori information enables computer 41 to invalidate vectors MM1 and MM2, which have negative x-axis components, and to determine that vectors TT1 and TT2 indeed correspond to the correct relative coordinate of tool 24 with respect to implant 26. Alternatively, location pads 34 can be marked and/or mounted using any other suitable method in order to fix a known orientation between at least one location pad and at least one position sensor. Other types of positional information relating to the position sensors and the location pads, can also be used.

Thus, following the two ambiguity resolution steps 124 and 126, computer 41 invalidates all but one of the potential relative vectors. The remaining vector corresponds to the correct relative coordinate of tool 24 with respect to implant 26.

In alternative embodiments, additional techniques can be used to exploit a-priori positional information to resolve the dipole measurement ambiguity. For example, the ambiguity can be resolved by placing two location pads at different distances from the implant along a particular axis, and on opposite sides of the axis. The absolute magnitude of the magnetic field sensed at the implant will be greater for the nearer location pad that for the more distant location pad. The ambiguity can be resolved by comparing the magnitudes of the field strengths generated by the two location pads. The a-priori positional information in this case comprises the known differences in the distance between the implant and the two location pads along the axis in question. This technique can be generalized to remove the measurement ambiguity in two or three dimensions.

In another alternative embodiment, an additional field generating coil can be located at a known distance from field generating coil 54 in one of location pads 34. The additional field generating coil is positioned so that its axis is parallel to the axis of coil 54 of the location pad. The relative coordinates of tool 24 with respect to implant 26 are then measured using each of the field generating coils, without ambiguity. The a-priori positional information in this case comprises the known relative location of the two coils.

In another embodiment, one of location pads 34 can be located further away from the working volume, so that the ambiguous location coordinates fall outside the predefined working volume. Limiting the measured coordinates to values that are within the working volume enables differentiating between true and mirror coordinates. The a-priori positional information in this case comprises the known boundaries of the working volume with respect to the distant location pad.

Ambiguity Resolution Using a Single Location Pad

In an alternative embodiment, the dipole field ambiguity can be resolved using a single location pad having multiple field generating coils.

Figure 7A:
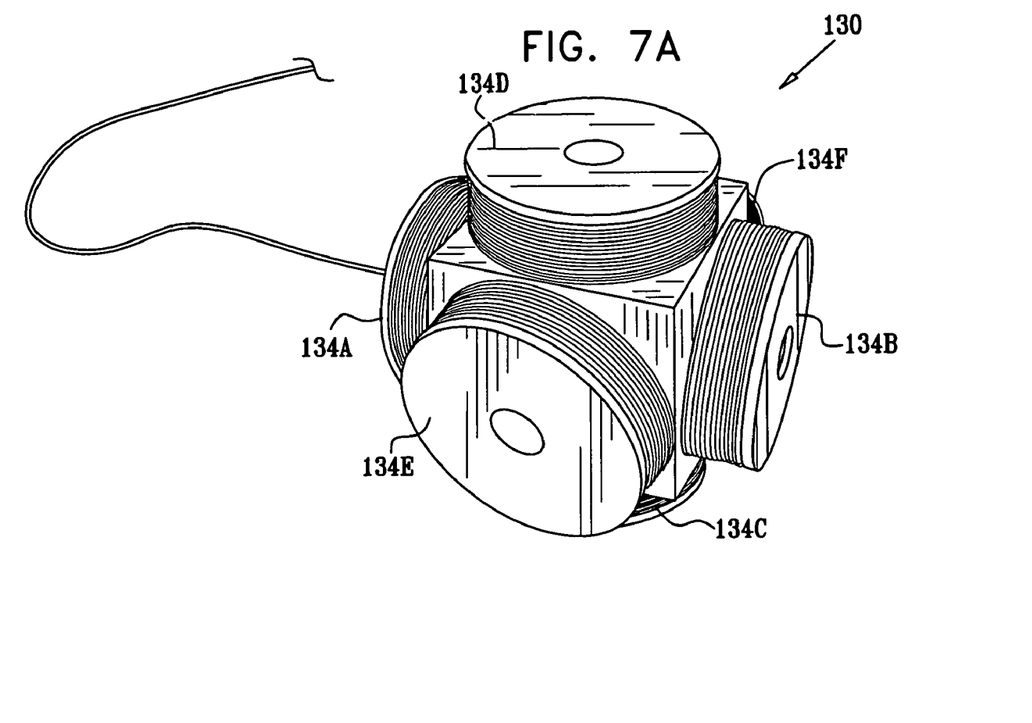
FIG. 7A is a schematic, pictorial illustration of a location pad, in accordance with another embodiment of the present invention.

FIG. 7A is a schematic, pictorial illustration of a location pad 130, in accordance with an embodiment of the present invention. Location pad 130 comprises six field generating coils 134A . . . 134F. The field generating coils are arranged in three pairs, with each coil pair oriented in a plane orthogonal to the other two pairs. In other words, two coils are oriented in the X-Y plane, two coils in the X-Z plane and two coils in the Y-Z plane. The coils are positioned at known offsets from the center of the location pad.

Figure 7B:
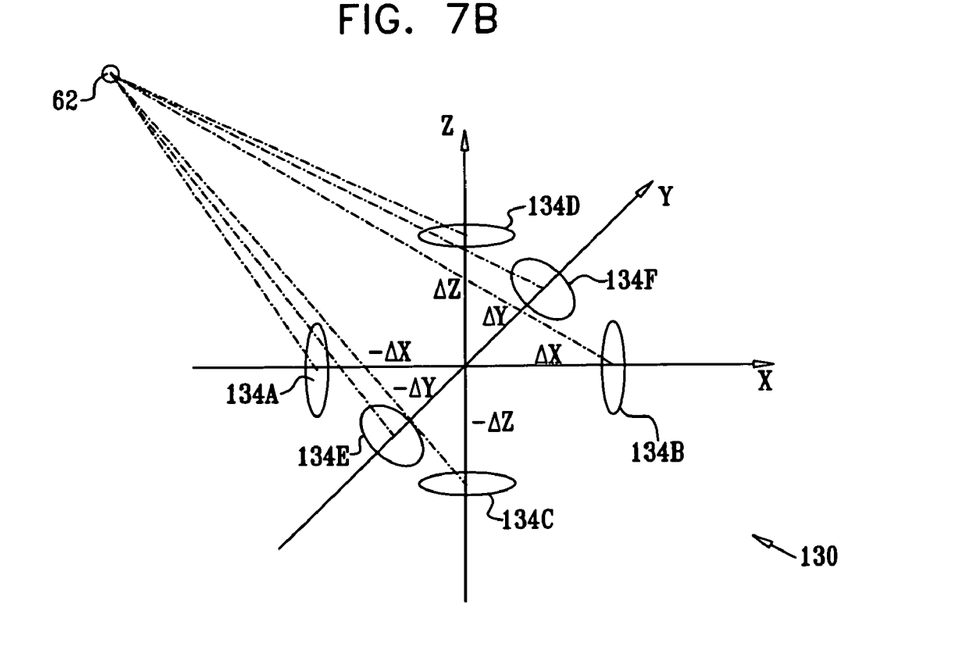
FIG. 7B is a diagram that schematically illustrates a method for resolving measurement ambiguity, in accordance with another embodiment of the present invention.

FIG. 7B is a diagram that schematically illustrates a method for resolving measurement ambiguity using location pad 130, in accordance with an embodiment of the present invention. The figure shows coils 134A . . . 134F of pad 130. Without loss of generality, the origin of the coordinate system is selected to be in the center of the location pad. The offsets of coils 134A . . . 134F from the origin are denoted $-\Delta x$, $\Delta x$, $-\Delta y$, $\Delta y$, $-\Delta z$ and $\Delta z$, respectively.

In the present example pad 130 is constructed so that all offsets are equal to one another and are on the order of 1 cm, although any other suitable configuration can be used. Additionally or alternatively, non-orthogonal coil configurations can also be used. Although the exemplary configuration of pad 130 comprises six field generating coils, any other suitable configuration of two or more coils having known mutual offsets can be used.

Sensor unit 62 shown in the figure may be fitted in implant 26, tool 24 or in any other suitable tracked object. Typically, the position coordinates of sensor unit 62 are measured with respect to each of coils 134A . . . 134F. Using the six measurements and the known values of the offsets of the coils with respect to the origin, the true position (location and orientation) coordinates of sensor unit 62 can be determined without ambiguity.

In some embodiments, the coils are driven by respective drive signals having different frequencies, and the different frequencies of the generated fields can be used to associate the position measurements with the appropriate coil. Alternatively, the coils can be driven one at a time in a time-division multiplexing (TDM) scheme. By synchronizing the position signals produced by sensor unit 62 with the TDM timing, each position measurement can be associated with the appropriate field generating coil.

Although the methods described herein addresses the calculation of a single relative coordinate, the method can be used to calculate relative coordinates among any number of position sensors associated with objects such as implants, medical instruments and tools.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. A method for position tracking, comprising:
    using a co-axial pair of first and second field generators fixed at a respective known offset from one another along a common axis in a location pad, generating respective first and second magnetic fields in a vicinity of an object;
    measuring the first and second magnetic fields using a position sensor associated with the object;
    calculating ambiguous position coordinates of the object with respect to the location pad based on the measured first and second magnetic fields using at least eight vectors;
    invalidating all position coordinates not similarly measured by first and second magnetic fields using the at least eight vectors; and
    calculating unambiguous position coordinates of the object with respect to the location pad from similarly measured position coordinates from the at least eight vectors based on the measured first and second magnetic fields and the known offset.

2. The method according to claim 1, and comprising generating additional magnetic fields using one or more additional co-axial pairs of field generators fixed at respective known offsets from one another along respective different axes, and measuring the additional magnetic fields by the position sensor, wherein calculating the unambiguous position coordinates comprises calculating the coordinates responsively to the measured additional magnetic fields and the respective known offsets.

3. The method according to claim 1, wherein generating the first and second magnetic fields comprises driving the first and second field generators with respective first and second drive signals having respective different first and second frequencies.

4. A position tracking system, comprising:
    a location pad comprising a co-axial pair of first and second field generators fixed at a known offset from one another along a common axis, which are arranged to generate respective first and second magnetic fields in a vicinity of an object;
    a position sensor associated with the object, which is arranged to measure the first and second magnetic fields; and
    a processor, which is arranged to calculate ambiguous position coordinates of the object with respect to the location pad based on the measured first and second magnetic fields using at least eight vectors and to invalidate all position coordinates not similarly measured by first and second magnetic fields using the at least eight vectors and to calculate unambiguous position coordinates of the object with respect to the location pad from similarly measured position coordinates from the at least eight vectors based on the measured first and second magnetic fields and the known offset.

5. The system according to claim 4, wherein the location pad comprises one or more additional co-axial pairs of field generators fixed at respective known offsets from one another along respective different axes, which are arranged to generate additional magnetic fields, wherein the position sensor is further arranged to measure the additional magnetic fields, and wherein the processor is arranged to calculate the unambiguous position coordinates responsively to the measured additional magnetic fields and the respective known offsets.

6. The system according to claim 4, wherein the first and second field generators are driven with respective first and second drive signals having respective different first and second frequencies.